United States Patent
Venkatesan et al.

(10) Patent No.: US 10,156,567 B2
(45) Date of Patent: Dec. 18, 2018

(54) IN-VITRO MAGNETIC RESONANCE DETECTION OF A TARGET SUBSTANCE WITHOUT SEPARATING BOUND MAGNETIC NANOPARTICLES FROM UNBOUND MAGNETIC NANOPARTICLES

(71) Applicant: General Electric Company, Schenectady, NY (US)

(72) Inventors: Ramesh Venkatesan, Bangalore (IN); Arun Balasubramanian, Bangalore (IN); Chandan Ramaswamy Atreya, Bangalore (IN); Ravi Hedge, Bangalore (IN); Ritika Uppal Mukherjee, Bangalore (IN)

(73) Assignee: General Electric Company, Schenectady, NY (US)

( * ) Notice: Subject to any disclaimer, the term of this patent is extended or adjusted under 35 U.S.C. 154(b) by 20 days.

(21) Appl. No.: 14/652,852

(22) PCT Filed: Dec. 13, 2013

(86) PCT No.: PCT/EP2013/076569
§ 371 (c)(1),
(2) Date: Jun. 17, 2015

(87) PCT Pub. No.: WO2014/095645
PCT Pub. Date: Jun. 26, 2014

(65) Prior Publication Data
US 2016/0195526 A1 Jul. 7, 2016

(30) Foreign Application Priority Data

Dec. 17, 2012 (IN) .......................... 3886/DEL/2012
Feb. 5, 2013 (GB) ................................. 1301992.2

(51) Int. Cl.
*G01N 24/08* (2006.01)
*G01N 33/569* (2006.01)
(Continued)

(52) U.S. Cl.
CPC . *G01N 33/56911* (2013.01); *G01N 33/54326* (2013.01); *G01N 33/54346* (2013.01);
(Continued)

(58) Field of Classification Search
CPC .... B82Y 25/00; A61K 49/0093; A61K 33/24; A61K 49/1827; A61K 49/1875;
(Continued)

(56) References Cited

U.S. PATENT DOCUMENTS 7,088,102 B1 8/2006 Zens
7,642,783 B2 1/2010 Freytag
(Continued)

FOREIGN PATENT DOCUMENTS

CN 101641352 A 2/2010
CN 104614513 A 5/2015
(Continued)

OTHER PUBLICATIONS

"Relaxation Time (T1 and T2) Measurements Bruker minispec Relaxation Time Manual", Aug. 2012, http://www.uni-ulm.de/physchem-praktikum/media/literatur/mq_Relaxation_Time_Manual.pdf.*
(Continued)

*Primary Examiner* — Arlen Soderquist

(57) ABSTRACT

The present invention provides an in-vitro method for detecting the presence of a target substance in a biological sample by magnetic resonance, the method comprising: a) providing a mixture comprising a biological sample and a plurality of magnetic nanoparticles, wherein the magnetic nanoparticles comprise a binding agent capable of binding (Continued)

the target substance when the target substance is present in the biological sample; and b) determining a $T_2$ relaxation time corresponding to magnetic nanoparticles that are bound to the target substance ($T_{2bound}$) in the sample; wherein $T_{2bound}$ differs from the $T_2$ relaxation time corresponding to the magnetic nanoparticles that are not bound to the target substance ($T_{2free}$), and wherein $T_{2bound}$ is determined without physically separating magnetic nanoparticles that are bound to the target substance from the magnetic nanoparticles that are not bound to the target substance.

11 Claims, 11 Drawing Sheets

(51) Int. Cl.
G01R 33/465 (2006.01)
G01N 33/543 (2006.01)
G01R 33/44 (2006.01)

(52) U.S. Cl.
CPC ......... *G01R 33/448* (2013.01); *G01R 33/465* (2013.01); *G01N 2333/32* (2013.01); *G01N 2469/10* (2013.01)

(58) Field of Classification Search
CPC ........ C12Q 2563/155; C12Q 2563/143; C12Q 2565/633; G01N 33/54326; G01N 33/54346; G01N 24/08; G01N 33/587; A61B 5/055; G01R 33/46
USPC .................................................. 436/63, 173
See application file for complete search history.

(56) References Cited

U.S. PATENT DOCUMENTS

| | | | | |
|---|---|---|---|---|
| 2003/0028093 | A1* | 2/2003 | Ke | A61B 5/055 600/410 |
| 2007/0111330 | A1 | 5/2007 | Hong et al. | |
| 2010/0301858 | A1* | 12/2010 | Lowery, Jr. | G01R 33/30 324/309 |
| 2010/0308822 | A1* | 12/2010 | Prado | G01N 24/08 324/309 |
| 2011/0262893 | A1 | 10/2011 | Dryga et al. | |
| 2012/0004530 | A1* | 1/2012 | Liu | G01R 33/50 600/410 |
| 2012/0100546 | A1 | 4/2012 | Lowery, Jr. et al. | |
| 2012/0164644 | A1* | 6/2012 | Neely | G01N 24/08 435/6.11 |
| 2012/0223705 | A1* | 9/2012 | Lowery | A61B 5/055 324/307 |
| 2013/0260367 | A1* | 10/2013 | Lowery, Jr. | B82Y 25/00 435/5 |
| 2014/0212901 | A1* | 7/2014 | Lowery, Jr. | G01N 24/08 435/13 |

FOREIGN PATENT DOCUMENTS

| | | |
|---|---|---|
| CN | 105920620 A | 9/2016 |
| EP | 2 385 386 A1 | 11/2011 |
| JP | 2008-542684 A | 11/2008 |
| JP | 2013-228280 A | 11/2013 |
| JP | 2014-095691 A | 5/2014 |
| WO | 2008057613 A2 | 5/2008 |
| WO | 2009045354 A1 | 4/2009 |
| WO | 2009045551 A1 | 4/2009 |
| WO | 2010109346 A1 | 9/2010 |
| WO | 2011120712 A1 | 10/2011 |
| WO | 201244387 A2 | 4/2012 |

OTHER PUBLICATIONS

MacKay, A. et al, Magnetic Resonance in Medicine 1994, 31, 673-677.*
Bulte, J. W. M. et al, Magnetic Resonance in Medicine 1997, 37, 530-536.*
Ke, Y. et al, Magnetic Resonance in Medicine 2002, 47, 232-238.*
Gossuin, Y. et al, Journal of Magnetic Resonance 2002, 158, 36-42.*
Sherwood, J. L. et al, Environmental Science and Technology 2003, 37, 781-785.*
Clark, P. R. et al, Magnetic Resonance Imaging 2003, 21, 519-530.*
Perez, J. M. et al, Journal of the American CHemical Society 2003, 125, 10192-10193.*
Snoussi, K. et al, Biophysical Journal 2005, 88, 2855-2866.*
Ghugre, N. R. et al, Magnetic Resonance in Medicine 2005, 54, 1185-1193.*
Kaittanis, C. et al, Nano Letters 2002, 7, 380-383.*
Taktak, S. et al, Analytical Chemistry 2007, 79, 8863-8869.*
Lowery, T. J. et al, Analytical Chemistry 2008, 80, 1118-1123.*
Koh, I. et al, Angewandte Chemie International Edition 2008, 47, 4119-4121.*
Lee, H. et al, Nature Medicine 2008, 14, 869-874.*
Novikov, D. S. et al, Journal of Magnetic Resonance 2008, 195, 33-39.*
Belotti, M. et al, Physical Chemistry Chemical Physics 2010, 12, 516-522.*
Ling, Y. "Nuclear Magnetic Resonance Readable Sensors" PhD Dissertation, 2010, 104 pages.*
Bannas, P. et al, Molecular Imaging 2010, 9, 211-222.*
Demas, V. et al, New Journal of Physics 2011, 13, paper 025005, 24 pages.*
Haun, J. B. et al, Science Translational Medicine 2011, 3, paper 71ra16, 13 pages plus supplimentary material.*
Issadore, D. et al, Lab on a Chip 2011, 11, 2282-2287.*
Horch, R. A. et al, Magnetic Resonance in Medicine 2012, 68, 1774-1784.*
Wen, S. et al, Journal of Lipid Research 2012, 53, 829-838.*
Cheng, H.-L. M. et al, Journal of Magnetic Resonance Imaging 2012, 36, 805-824.*
Perez, J. M. et al, ChemBioChem 2004, 5, 261±264.*
Haun, J. B. et al, WIREs Nanomedicine and Nanobiotechnology 2010, 2, 291-304.*
Hakho Lee et al: "Ultrasensitive Detection of Bacteria Using Core-Shell Nanoparticles and an NMR-Filter System", Angewandte Chemie (International Ed. in English), vol. 121, No. 31, Jul. 20, 2009 (Jul. 20, 2009), pp. 5767-5770, XP055101008, ISSN: 0044-8249, DOI: 10.1002/ange.200901791 cited in the application the whole document.
Shao H et al: "Magnetic nanoparticles for biomedical NMR-based diagnostics", Beilstein Journal of Nanotechnology 2010 Beilstein-Institut Forderung Der Chemischen Wissenschaft Deu, vol. 1, No. 1, 2010, pp. 142-154, XP002723350, DOI: 10.3762/BJNAN0.1.1. 17 cited in the application the whole document.
International Search Report dated Apr. 30, 2014 which was issued in connection with PCT Patent Application No. PCT/EP2013/076569 which was filed on Dec. 13, 2013.
GB Search Report dated May 2, 2013 which was issued in connection with GB Patent Application No. 1301992.2 which was filed on Feb. 5, 2013.
Chinese Office Action for 201380065739.4 dated Mar. 15, 2017 and English Translation of the same, 39 pages.
Balasubramanian, A. et al., A micro-magnetic resonance system for detecting presence of cell in a fluid sample, GE Co-Pending Application No. 3407/CHE/2011, filed on Sep. 30, 2011.
Hou, T. et al., "Analysis of Multiple Samples Using Multiplex Sample NMR: Selective Excitation and Chemical Shift Imaging Approaches," Analytical Chemistry, vol. 73, No. 11, pp. 2541-2546 (2001).
Machine translation and Decision to Grant issued in connection with corresponding JP Application No. 2015-547053 dated Jun. 19, 2018.

* cited by examiner

IN-VITRO MAGNETIC RESONANCE DETECTION OF A TARGET SUBSTANCE WITHOUT SEPARATING BOUND MAGNETIC NANOPARTICLES FROM UNBOUND MAGNETIC NANOPARTICLES

TECHNICAL FIELD

The subject matter disclosed herein relates to an in-vitro method of detecting target substances, for examples cells or pathogens, in biological samples using magnetic resonance.

BACKGROUND OF THE INVENTION

The detection of clinically relevant substances in biological samples, such as cells and pathogens, is important in the field of diagnostics. Many traditional detection strategies are based on optical techniques. However, such techniques are often affected by deleterious effects such as light scattering, absorption and autofluorescence. Minimizing such effects can require extensive sample purification prior to the recording measurements.

Detection strategies employing magnetic nanoparticles offer unique advantages over traditional detection methods. For example, biological samples exhibit negligible magnetic background, and so the use of magnetic nanoparticles provides the opportunity to obtain very sensitive measurements in samples without subjecting the samples to significant pre-processing steps.

A magnetic nanoparticle may be comprised of an inorganic magnetic core and a biocompatible surface coating that stabilizes the particle in physiological conditions. By applying suitable surface chemistry, functional ligands can be incorporated onto the nanoparticle in order to confer molecular specificity.

When magnetic nanoparticles are placed in an external field, each particle creates a local magnetic field, which increases the field inhomogeneity. This has the effect of perturbing the coherent precessions of water proton spins when water molecules diffuse in the proximity of the nanoparticles. As a consequence, the net effect is a change in the magnetic resonance signal, which is measured as a shortening of the longitudinal (T1, spin-lattice) and transverse (T2, spin-spin) relaxation times.

The term "$T_2$" refers to the spin-spin relaxation time constant characterizing the signal decay, and can be represented by the equation $$M_{xy}(t) = M_{xy}(0) e^{-t/T2}$$

where $M_{xy}$ is the transverse component of the magnetization vector tipped down by a radiofrequency (RF) pulse.

Magnetic nanoparticles have previously been used to detect biological targets such as bacteria and mammalian cells. Target-specific magnetic nanoparticles are used which tag cell-surface biomarkers, thereby imparting a magnetic moment. The increase in the relaxation rate $R_2 = 1/T_2$ is directly proportional to the number of nanoparticles bound to a target (and also indicative of the amount of marker surface markers). The change of $R_2$ and hence $T_2$ can therefore be used to detect the presence of cells in a sample solution (Shao et al., Beilstein J. Nanotechnol; (2010); 1; pages 142-154). However, the methods described in the prior art require removal of unbound magnetic nanoparticles to ensure sensitivity of the assay, which is typically achieved by filtration. Where detection has been achieved by employing a micro-MR device, the device requires a filtration membrane at the end of the reaction flow pathways for unbound magnetic nanoparticles to be filtered out (Lee et al., Angew Chem Int Ed Engl; (2009); 48; pages 5657-5660).

The need to remove unbound magnetic nanoparticles from the bound magnetic nanoparticles gives rise to a number of problems. For example, employing a microfluidics network and filtration membrane add to the cost of MR detection devices. The additional filtration step can also increase the cost of sample preparation, a factor which is particular significant in developing countries where affordable testing techniques are paramount. Furthermore, the need for an additional separation step exposes the technician performing the diagnostic test to potentially hazardous substances.

BRIEF DESCRIPTION OF THE INVENTION

The present invention relates to an in-vitro method for detecting the presence of a target substance in a sample by magnetic resonance, the method comprising:

(a) providing a test sample comprising a biological sample;

(b) providing a plurality of magnetic nanoparticles, wherein said magnetic nanoparticles comprise a binding agent capable of binding the target substance;

(c) contacting the test sample with the plurality of magnetic nanoparticles to provide a mixture containing the magnetic nanoparticles and the test sample; and (d) determining a $T_2$ relaxation time corresponding to magnetic nanoparticles that are bound to the target substance ($T_{2bound}$) in the sample;

wherein $T_{2bound}$ differs from the $T_2$ relaxation time corresponding to the magnetic nanoparticles that are not bound to the target substance ($T_{2free}$), and wherein $T_{2bound}$ is determined without physically separating magnetic nanoparticles that are bound to the target substance from the magnetic nanoparticles that are not bound to the target substance.

The present invention also provides an in-vitro method for detecting for the presence of a target substance in a biological sample by magnetic resonance, the method comprising:

(a) providing a mixture comprising a biological sample and a plurality of magnetic nanoparticles, wherein the magnetic nanoparticles comprise a binding agent capable of binding the target substance when the target substance is present in the biological sample; and (b) determining a $T_2$ relaxation time corresponding to magnetic nanoparticles that are bound to the target substance ($T_{2bound}$) in the sample;

wherein $T_{2bound}$ differs from the $T_2$ relaxation time corresponding to the magnetic nanoparticles that are not bound to the target substance ($T_{2free}$), and wherein $T_{2bound}$ is determined without physically separating magnetic nanoparticles that are bound to the target substance from the magnetic nanoparticles that are not bound to the target substance.

The present invention also provides a method for detecting the presence of a target substance in a biological sample, the method comprising:

(a) providing NMR data from a mixture comprising a biological sample and a plurality of magnetic nanoparticles, wherein the magnetic nanoparticles comprise a binding agent capable of binding the target substance when the target substance is present in the biological sample; and (b) determining from the NMR data a $T_2$ relaxation time corresponding to magnetic nanoparticles that are bound to the target substance ($T_{2bound}$) in the sample;

wherein $T_{2bound}$ differs from the $T_2$ relaxation time corresponding to the magnetic nanoparticles that are not bound to the target substance ($T_{2free}$), and wherein $T_{2bound}$ is differentiated from $T_{2free}$ by processing of the NMR data to obtain separate values of $T_{2bound}$ and $T_{2free}$.

The present invention also provides an in-vitro method for detecting the presence of a target substance in a biological sample by magnetic resonance, the method comprising:

(a) providing a mixture comprising a biological sample and a plurality of magnetic nanoparticles, wherein the magnetic nanoparticles comprise a binding agent capable of binding the target substance when the target substance is present in the biological sample; and (b) determining a T2 relaxation time corresponding to magnetic nanoparticles that are bound to the target substance ($T_{2bound}$) in the sample;

wherein $T_{2bound}$ differs from the $T_2$ relaxation time corresponding to the magnetic nanoparticles that are not bound to the target substance ($T_{2free}$), and wherein $T_{2bound}$ is differentiated from $T_{2free}$ by processing of NMR data to obtain separate values of $T_{2bound}$ and $T_{2free}$.

The present invention also provides a method for detecting for the presence of a target substance in a biological sample, the method comprising:

(a) providing NMR data from a mixture comprising a biological sample and a plurality of magnetic nanoparticles, wherein the magnetic nanoparticles comprise a binding agent capable of binding the target substance when the target substance is present in the biological sample; and (b) processing the NMR data to determine if different $T_2$ values corresponding to $T_{2bound}$ and $T_{2free}$ are present, wherein $T_{2bound}$ is the $T_2$ relaxation time corresponding to magnetic nanoparticles that are bound to the target substance if present, and $T_{2free}$ is the $T_2$ relaxation time corresponding to magnetic nanoparticles that are not bound to the target substance.

In an embodiment, the biological sample is a sample obtained from a mammalian subject, more particularly a human, such as an individual suspected of having a disease or infection. The target substance, which may be, for example, a cell or pathogen, may represent a target that is indicative of the disease or infection.

The present invention thus relates to a method of detecting a target substance in a biological sample, such as cells or pathogens, using magnetic nanoparticles without the need for physically separating/filtering the magnetic nanoparticles that are bound to the target substance from the nanoparticles that are not bound to the target substance.

The present inventors have further established that the value for $T_{2bound}$ is dependent on the concentration of target substance (e.g. cells, pathogen or bacteria) and so the determination of $T_{2bound}$ can enable the determination of the amount (e.g. number of concentration) of target substance.

Thus, the present invention has clear advantages over prior art methods which require the above-mentioned separation step. For example, the removal of this step reduces the time and cost of sample preparation. Removal of this step can also reduce the exposure of a technician performing the test to an otherwise potentially hazardous sample. Moreover, the need for highly-trained manpower can be eliminated.

In an embodiment of the invention, the target substance is a cell and/or a pathogen, such as a bacterial cell.

In a further embodiment, $T_{2bound}$ is differentiated from $T_{2free}$ by signal processing of NMR data to obtain separate values of $T_{2bound}$ and $T_{2free}$. In an embodiment, the signal processing comprises applying a bi-exponential fit to the NMR data obtained from the mixture to obtain separate values of $T_{2bound}$ and $T_{2free}$.

In a further embodiment, the mixture is subjected to a spin-echo pulse sequence, in particular a multi-echo spin echo pulse sequence.

In a yet further embodiment, the method according to the invention further comprises quantitating the amount of target substance in the sample or mixture. In an aspect of this embodiment, the value of $T_{2bound}$ is dependent on the amount of target substance in the mixture, and the amount of target substance is determined by comparing the value of $T_{2bound}$ with a standard plot of $T_{2bound}$ values measured at different concentrations of target substance. Additionally, or alternatively, the value of $T_{2bound}$ is dependent on the amount of target substance in the mixture, and the value of $T_{2bound}$ is compared to one or more standard values obtained from reference samples comprising known amounts of target substance.

In a further embodiment, the method of the present invention is carried out on a micro-MR device.

In a further embodiment, the magnetic nanoparticles comprise superparamagnetic particles conjugated to a binding agent. Each magnetic particle may comprise a core comprising superparamagnetic iron oxide (SPIO), wherein the particles are conjugated to a binding agent.

In a further embodiment, the binding agent is an antibody or an antibody fragment comprising a binding site specific for the target substance.

DETAILED DESCRIPTION OF THE INVENTION

Figure 1:
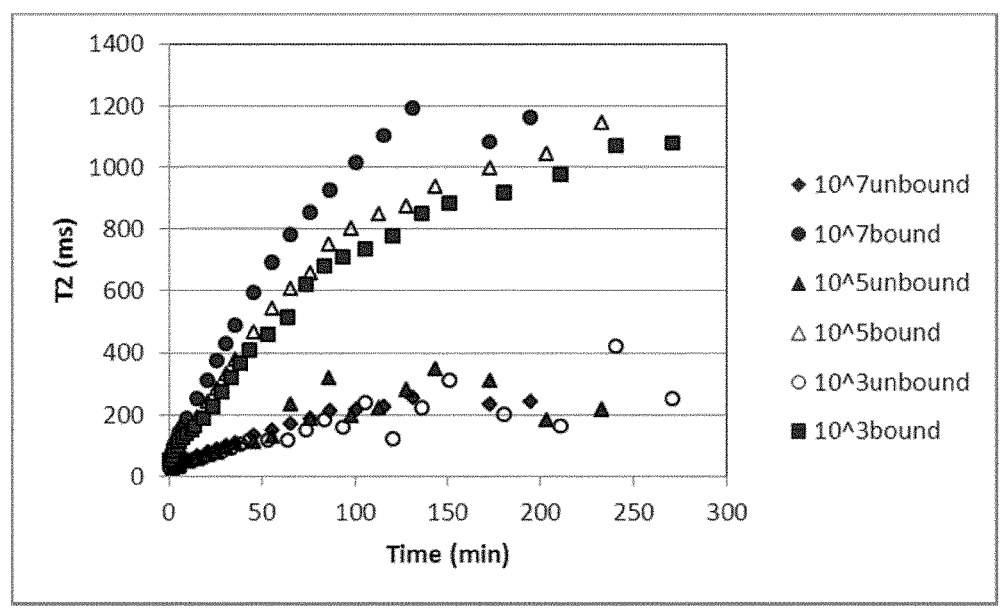
FIG. 1 is a plot showing the T2 relaxation time vs time for a reaction between bacteria-targeting magnetic nanoconjugates and bacteria.

The present invention provides an in-vitro method for detecting the presence of a target substance in a sample by magnetic resonance, the method comprising:

providing a test sample comprising a biological sample;

providing a plurality of magnetic nanoparticles, wherein said magnetic nanoparticles comprise a binding agent capable of binding the target substance;

contacting the test sample with the plurality of magnetic nanoparticles to provide a mixture containing the magnetic nanoparticles and the test sample;

determining a $T_2$ relaxation time corresponding to magnetic nanoparticles that are bound to the target substance ($T_{2bound}$) in the sample;

wherein $T_{2bound}$ differs from the $T_2$ relaxation time corresponding to the magnetic nanoparticles that are not bound to the target substance ($T_{2free}$), and wherein $T_{2bound}$ is determined without physically separating magnetic nanoparticles that are bound to the target substance from the magnetic nanoparticles that are not bound to the target substance.

The present invention also provides an in-vitro method for detecting for the presence of a target substance in a biological sample by magnetic resonance, the method comprising:

providing a mixture comprising a biological sample and a plurality of magnetic nanoparticles, wherein the magnetic nanoparticles comprise a binding agent capable of binding the target substance when the target substance is present in the biological sample; and determining a $T_2$ relaxation time corresponding to magnetic nanoparticles that are bound to the target substance ($T_{2bound}$) in the sample;

wherein $T_{2bound}$ differs from the $T_2$ relaxation time corresponding to the magnetic nanoparticles that are not bound to the target substance ($T_{2free}$), and wherein $T_{2bound}$ is determined without physically separating magnetic nanoparticles that are bound to the target substance from the magnetic nanoparticles that are not bound to the target substance.

The present invention also provides a method for detecting the presence of a target substance in a biological, the method comprising:

providing NMR data from a mixture comprising a biological sample and a plurality of magnetic nanoparticles, wherein the magnetic nanoparticles comprise a binding agent capable of binding the target substance when the target substance is present in the biological sample; and determining from the NMR data a $T_2$ relaxation time corresponding to magnetic nanoparticles that are bound to the target substance ($T_{2bound}$) in the sample;

wherein $T_{2bound}$ differs from the $T_2$ relaxation time corresponding to the magnetic nanoparticles that are not bound to the target substance ($T_{2free}$), and wherein $T_{2bound}$ is differentiated from $T_{2free}$ by processing of NMR data to obtain separate values of $T_{2bound}$ and $T_{2free}$.

The present invention also provides an in-vitro method for detecting the presence of a target substance in a biological sample by magnetic resonance, the method comprising:

providing a mixture comprising a biological sample and a plurality of magnetic nanoparticles, wherein the magnetic nanoparticles comprise a binding agent capable of binding the target substance when the target substance is present in the biological sample; and determining a $T_2$ relaxation time corresponding to magnetic nanoparticles that are bound to the target substance ($T_{2bound}$) in the sample; where $T_{2bound}$ refers to $T_2$ spin-spin relaxation time of protons of water molecules surrounding the magnetic nanoparticles that are bound to the target substance, wherein $T_{2bound}$ differs from the $T_2$ relaxation time corresponding to the magnetic nanoparticles that are not bound to the target substance ($T_{2free}$), and wherein $T_{2bound}$ is determined without physically separating magnetic nanoparticles that are bound to the target substance from the magnetic nanoparticles that are not bound to the target substance. Here $T_{2free}$ refers to $T_2$ spin-spin relaxation time of protons of water molecules surrounding the magnetic nanoparticles that are not bound to the target substance.

The present invention also provides a method for detecting for the presence of a target substance in a biological sample, the method comprising:

providing NMR data from a mixture comprising a biological sample and a plurality of magnetic nanoparticles, wherein the magnetic nanoparticles comprise a binding agent capable of binding the target substance when the target substance is present in the biological sample; and processing the NMR data to determine if different $T_2$ values corresponding to $T_{2bound}$ and $T_{2free}$ are present, wherein $T_{2bound}$ is the $T_2$ relaxation time corresponding to magnetic nanoparticles that are bound to the target substance if present, and $T_{2free}$ is the $T_2$ relaxation time corresponding to magnetic nanoparticles that are not bound to the target substance.

When magnetic nanoparticles are placed in an external field, each particle creates a local magnetic field, which increases the field inhomogeneity. This has the effect of perturbing the coherent precession of water proton spins when water molecules diffuse in the proximity of the nanoparticles. As a consequence, the net effect is a change in the magnetic resonance signal, which is measured as a shortening of the longitudinal ($T_1$, spin-lattice) and transverse ($T_2$, spin-spin) relaxation times.

The present inventors have identified that the $T_2$ relaxation value associated with magnetic nanoparticles is reduced when the magnetic nanoparticles are bound to a target substance, such as a cell. More particularly, the present inventors have demonstrated that when magnetic nanoparticles comprising a binding agent specific to a target substance, such as a cell type, are incubated in the presence of the target substance (e.g. a target cell), two $T_2$ measurements are obtainable. The first $T_2$ value (typically the lower value) corresponds to the $T_2$ value that is associated with the nanoparticles that are not bound to the substance (referred to herein as $T_{2free}$). The second $T_2$ value (typically the higher value) corresponds to the $T_2$ value that is associated with the nanoparticles that are bound to substance (referred to herein as $T_{2bound}$).

The present inventors have further identified that it is possible to measure the values of $T_{2free}$ and $T_{2bound}$ in a mixture of the target substrate (e.g. cells) and the magnetic nanoparticles without physically separating the nanoparticles that are not bound to the target substrate (e.g. cells). This can be achieved by processing NMR data from the mixture to obtain a value for both $T_{2free}$ and $T_{2bound}$. In an embodiment, the processing step comprises applying a bi-exponential fit to the NMR data obtained from the mixture. The bi-exponential fit caters for the fact that two distinct $T_2$ values may exist in the mixture being subjected to an NMR measurement experiment.

An example of a bi-exponential fit equation that may be used to determine values for $T_{2free}$ and $T_{2bound}$ is shown in equation (1) below:

$$y = A1 * \exp-(x/\tau 1) + A2 * \exp-(x/\tau 2) + O \quad \text{(equation 1)}$$

where:
A1, A2=amplitudes of components 1 and 2 at time zero
$\tau 1$, $\tau 2$=T2 decay constants of components 1 and 2
O=offset Typically, such nonlinear fits are performed in an iterative fashion using, for example, a Levenberg-Marquardt nonlinear least-squares fitting algorithm. The iterative process is initiated with a guess of the unknowns. In this case, the unknowns are the relative amplitudes A1, A2, the relaxation times $_1$ and $_2$ as well as the offset O. All of these are determined by the algorithm, which has a stopping criterion for its iterative process. Such a fitting algorithm is available as a standard routine on most commercially available relaxometers, In the NMR determination of the $T_2$ values, the $T_2$ values can be determined using NMR signals acquired during the application of a suitable pulse sequence to the sample. In an embodiment, the sequence is a multi-echo spin-echo pulse sequence.

An example of a suitable sequence is the Carr-Purcell-Meiboom-Gill (CPMG) spin echo sequence:

$$\{RD\ \text{-}90_0\text{-tau-}[(180_{90}\text{-tau-})DE(180_{90}\text{-tau-})asd\text{-tau-}]_N\}_{NS}$$

where:
RD is the recycle delay, tau is a delay interval, DE is the number of dummy echoes before an echo is sampled, N is the number of points to be collected, NS is the number of scans for signal averaging and "asd" is indicative of acquisition of a single data point.
Example parameters are: RD=6 s; tau=5 ms, DE=0, N=700, NS=8. However, it will be appreciated that a skilled person could readily determine other sequences that may be used in the present invention that allow the determination of $T_2$ values.

The present inventors have further established that the value for $T_{2bound}$ is dependent on the concentration of target substance (e.g. cells, pathogen or bacteria). The present invention may therefore be further used to quantitate the amount of target substance (e.g. number or concentration of cells, pathogen or bacteria) that may be present in the sample without the need to filter the unbound nanoconjugates.

Accordingly, in an embodiment, the value of $T_{2bound}$ is dependent on the amount of target substance in the test sample/mixture, and the amount of target substance in the test sample is determined by comparing the value of $T_{2bound}$ with a standard plot of $T_{2bound}$ values measured at different concentrations of target substance.

In a further embodiment, the value of $T_{2bound}$ is dependent on the amount of target substance in the sample, and the value of $T_{2bound}$ is compared to one or more standard values obtained from reference samples comprising known amounts of target substance.

Figure 2:
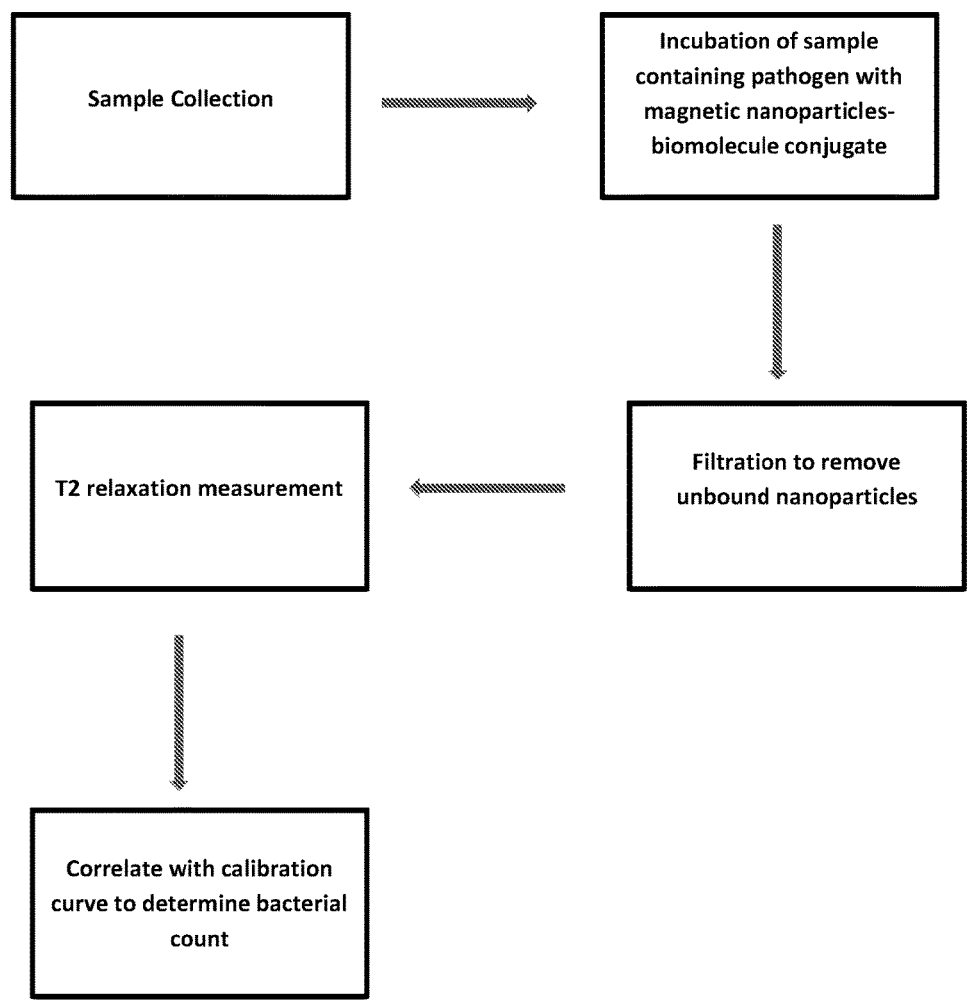
FIG. 2 is a schematic illustration of a process for detection of target substance employing a filtration step.
Figure 3:
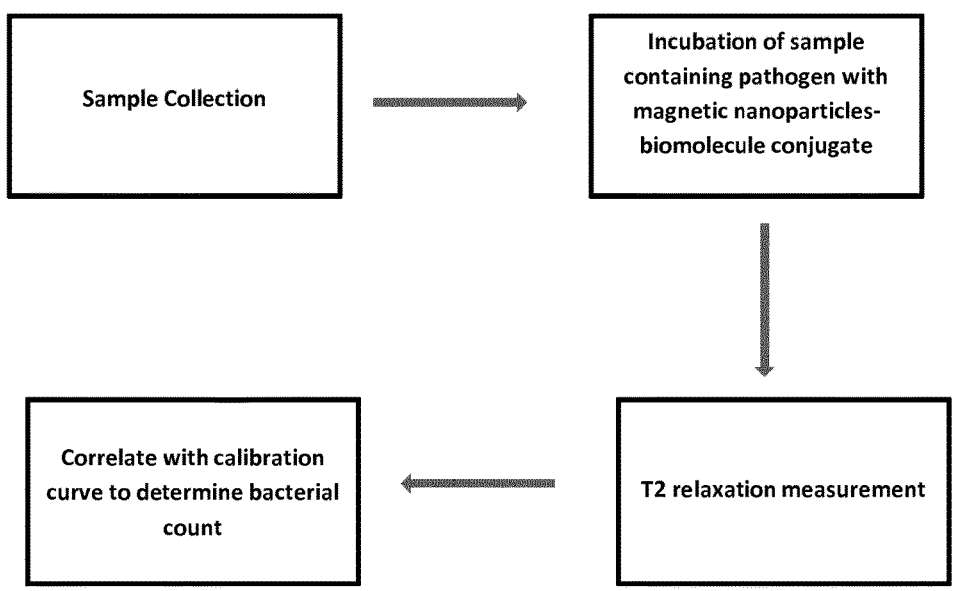
FIG. 3 is a schematic illustration of a process for detection of a target substance using a method of the present invention, where a filtration step is not required.

The advantages brought about by the present invention can be appreciated by comparing the schematic workflow shown on FIG. 2 with that of FIG. 3. FIG. 2 is a schematic illustration of a process for detection of a target substance employing a filtration step. FIG. 3 is a schematic illustration of a process for detection of a target substance using the method of the present invention, where a filtration step is not a necessary requirement.

Throughout this application, reference is made to determining $T_2$ values. However, it is appreciated that since $T_2=1/R_2$ (where $R_2$ is the relaxation rate constant), the method of the present invention can be carried out by determining $R_2$. Accordingly, determining the presence and/or amount of target substance in a sample by determining $R_2$ values (e.g. $R2_{bound}$ and $R2_{free}$) is intended to be within the scope of the present invention since $R_2$ is the reciprocal of $T_2$. For example, determination of $R_2$ values can be made by replacing the $T_2$ constants in equation 1 with $1/R_2$. Accordingly, detecting the presence of target substances by detecting values of $R2_{bound}$ and $R2_{free}$ is within the scope of the present invention since references herein to determining a $T_2$ value can also be considered to be the determination of the corresponding $R_2$ value and vice-versa.

Magnetic nanoparticles that may be employed in the present invention are well known in the art. The nanoparticles include, but are not limited to, magnetic or superparamagnetic nanoparticles. The nanoparticles can act as proximity sensors that modulate the spin-spin relaxation time of neighboring molecules which can be measured using MRI and other NMR relaxometers. The nanoparticles are suitably physically and chemically stable, biocompatible and environmentally safe.

The magnetic nanoparticles should ideally have a strong magnetic moment to induce pronounced $T_2$ changes whilst also exhibiting superparamagnetic behavior to avoid spontaneous magnetic aggregation. Furthermore, the nanoparticles should be coated with a suitable coating to prevent aggregation in aqueous solution. Suitable coatings are typically hydrophilic and biocompatible. In an embodiment, the coating should provide a means to attach one or more binding agents such as antibodies, DNA, proteins peptides or small molecules.

Examples of magnetic nanoparticles include cross-linked iron oxide (CLIO) nanoparticles, aminated CLIO (amino-CLIO) nanoparticles, manganese-doped iron oxide magnetic nanoparticles, superparamagnetic iron oxide (SPIO) particles, and elemental iron core/ferrite shell nanoparticles. Such nanoparticles can be suitably coated as described above. Examples of magnetic nanoparticles, and their use in in-vitro nuclear magnetic resonance detection, are provided in the publication entitled "*Magnetic Nanoparticle Biosensors*", authored by Jered B. Haun, Tae-Jong Yoon, Hakho Lee and Ralph Weissleder (published in Wiley Interdisciplinary Reviews: Nanomedicine and Nanobiotechnology; Vol. 2; Issue 3; May/June 2010; Pages 291-304). Further examples are provided, for example, in the publication entitled "*Magnetic Resonance for In-Vitro Medical Diagnostics: Superparamagnetic Nanoparticle-Based Magnetic Relaxation Switches*", authored by Vasiliki Demas and Thomas J Lowery (published in New Journal of Physics: Volume 13, Issue 2 (2011), pp. 025005).

In order for the nanoparticles to bind to the target substance, the nanoparticles may be labeled or conjugated to binding agents that are specific for the target substance (e.g. cell, pathogen or bacterium). The nature and structure of the binding agent will depend on the nature of the target to be detected. Examples of such binding agents include: an antibody that recognizes and binds a target moiety on the target substance; an oligonucleotide or DNA sequence complementary to a DNA- or RNA-target; a DNA- or RNA-aptamer that e.g. binds to a target protein, bacteria, virus, yeast or fungus; a protein or peptide that e.g. binds to a target protein, bacteria, virus, yeast or fungus; a peptide comprising unnatural amino acids which may possess enhanced binding to a target and/or possess improved environmental stability; a small molecule or combination of small molecules that can bind to a target. The moiety can be linked to the nanoparticle (e.g. the shell of the nanoparticle) by covalent or non-covalent bond(s). The moiety can be linked to the nanoparticle by a suitable functional group. Suitable functional groups can include —O—, —S—, —SS—, —NH—, —NHC(O)—, —(O)CNH—, —NHC(O)(CH2)nC(O)—, —O)C(CH2)nC(O)NH—, —NHC(O)(CH2)nC(O)NH—, —C(O)O—, —OC(O)—, —NHNH—, —C(O)S—, —SC(O)—, —OC(O)(CH2)n(O)—, —O(CH2)nC(O)O—, —OC(O)(CH2)nC(O)—, —C(O)(CH2)nC(O)O—, —C(O)(CH2)nC(O)—, —NH(CH2)nC(O)—, —C(O)(CH2)nNH—, —O(CH2)nC(O)—, —C(O)(CH2)nO—, —C(O)(CH2)nC(O)—, —C(O)(CH2)nS—, —NH(CH2)n-, —(CH2)nNH—, —O(CH2)n-, —(CH2)nO—, —S(CH2)n-, or —(CH2)nS—, in which each n can be 1-100 (e.g., n can be 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, 99). Methods of conjugating binding agents to nanoparticles are well known in the art, examples of which are provided in the above mentioned publications. Further examples are provided, for example, in U.S. Pat. No. 7,829,350 B2.

In an embodiment, the binding agent is an antibody. The term "antibody" describes an immunoglobulin whether natural or partly or wholly synthetically produced. The antibody may be monoclonal or polyclonal and may be prepared by techniques that are well-known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. The term "antibody" also covers any polypeptide or protein comprising an antibody antigen-binding site. Antibody fragments that comprise an antibody antigen-binding site include, but are not limited to molecules such as Fab, Fab', Fab'-SH, scFv, Fv, dAb, Fd; and diabodies.

The target substance is a substance that may be present in the biological sample to be tested and for which knowledge of the presence of the target substance is desired e.g. to reach a clinical diagnosis. Examples of target substances include cells (e.g. cells expressing particular biomarkers of interest), bacteria, pathogens, viruses, parasites, yeast or fungus.

Examples of bacteria that can be detected by the present invention include Gram-positive bacteria e.g. *Staphylococcus aureus* or *Bacillus subtilis*; Gram-negative bacteria e.g. *Escherichia coli* or *Pseudomonas aeruginosa*; and acid-fast bacilli e.g. strains of mycobacteria, such as *Mycobacterium tuberculosis*.

Examples of pathogens that can be detected by the present invention include bacteria, fungi, parasites, yeast and viruses.

Examples of cells that can be detected by the present invention include bacteria, tumor cells, stem cells, mammalian cells and other cells.

The binding agent on the magnetic nanoparticles is capable of specifically binding to the target substance of interest. The binding agent will typically bind to a target site on the target substance. The target site may, for example, be a biomarker that characterizes the target substance.

The target site may include a target protein. A target protein according to an embodiment of the invention may be present on the surface of the target substance. In some embodiments, a target protein may not be inherently present on the surface of a biological sample and the biological sample may have to be processed to make the target protein available on the surface. In some embodiments, the target protein may be in a tissue, either on a cell surface, or within a cell.

In some embodiments, a target site (e.g. protein) may provide information about the presence or absence of a target substance in the biological sample. In another embodiment, a target protein may provide information on a state of a biological sample. For example, if the methods disclosed herein may be used to detect target protein that may help in comparing different types of cells, comparing different developmental stages, detecting the presence of a disease or abnormality, or determining the type of disease or abnormality.

Suitable target proteins may include one or more of peptides, proteins (e.g., antibodies, affibodies, or aptamers), enzymes, ligands, receptors, antigens, or haptens. One or more of the aforementioned target proteins may be characteristic of particular cells, while other target proteins may be associated with a particular disease or condition. In some embodiments, target proteins present on target substances (e.g. cells, bacteria or pathogens) in a sample that may be detected and analyzed using the methods disclosed herein may include, but are not limited to, prognostic markers, predictive markers, hormone or hormone receptors, lymphoids, tumor markers, cell cycle associated markers, neural tissue and tumor markers, or cluster differentiation markers.

Suitable examples of prognostic markers may include enzymatic targets such as galactosyl transferase II, neuron specific enolase, proton ATPase-2, or acid phosphatase. Other examples of prognostic protein or gene markers include Ki67, cyclin E, p53, cMet.

Suitable examples of predictive markers (drug response) may include protein or gene targets such as EGFR, Her2, ALK.

Suitable examples of hormone or hormone receptors may include human chorionic gonadotropin (HCG), adrenocorticotropic hormone, carcinoembryonic antigen (CEA), prostate-specific antigen (PSA), estrogen receptor, progesterone receptor, androgen receptor, gClq-R/p33 complement receptor, IL-2 receptor, p75 neurotrophin receptor, PTH receptor, thyroid hormone receptor, or insulin receptor.

Suitable examples of lymphoids may include alpha-1-antichymotrypsin, alpha-1-antitrypsin, B cell target, bcl-2, bcl-6, B lymphocyte antigen 36 kD, BM1 (myeloid target), BM2 (myeloid target), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage target, muramidase (lysozyme), p80 anaplastic lymphoma kinase, plasma cell target, secretory leukocyte protease inhibitor, T cell antigen receptor (JOVI 1), T cell antigen receptor (JOVI 3), terminal deoxynucleotidyl transferase, or unclustered B cell target.

Suitable examples of tumor markers may include alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, gross cystic disease fluid protein-15, hepatocyte specific antigen, heregulin, human gastric mucin, human milk fat globule, MAGE-1, matrix metalloproteinases, melan A, melanoma target (HMB45), mesothelin, metallothionein, microphthalmia transcription factor (MITF), Muc-1 core glycoprotein. Muc-1 glycoprotein, Muc-2 glycoprotein, Muc-5AC glycoprotein, Muc-6 glycoprotein, myeloperoxidase, Myf-3 (Rhabdomyosarcoma target), Myf-4 (Rhabdomyosarcoma target), MyoD1 (Rhabdomyosarcoma target), myoglobin, nm23 protein, placental alkaline phosphatase, prealbumin, prostate specific antigen, prostatic acid phosphatase, prostatic inhibin peptide, PTEN, renal cell carcinoma target, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, or von Willebrand factor.

Suitable examples of cell cycle associated markers may include apoptosis protease activating factor-1, bcl-w , bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mcl-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, or topoisomerase II beta.

Suitable examples of cluster differentiation markers may include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79A, CD79B, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, and TCR-zeta.

Other suitable target proteins include centromere protein-F (CENP-F), giantin, involucrin, lamin A&C (XB 10), LAP-70, mucin, nuclear pore complex proteins, p180 lamellar body protein, ran, cathepsin D, Ps2 protein, Her2-neu, P53, S100, epithelial target antigen (EMA), TdT, MB2, MB3, PCNA, Ki67, cytokeratin, PI3K, cMyc or MAPK.

Still other suitable target proteins include Her2/neu (epidermal growth factor over expressed in breast and stomach cancer, therapy by a monoclonal antibody slows tumor growth); EGF-R/erbB (epidermal growth factor receptor); ER (estrogen receptor required for growth of some breast cancer tumors, located in the nucleus and detected with ISH for deciding on therapy limiting estrogen in positive patients); PR (progesterone receptor is a hormone that binds to DNA); AR (androgen receptor is involved in androgen dependent tumor growth); β-catenin (oncogene in cancer translocates from the cell membrane to the nucleus, which functions in both cell adhesion and as a latent gene regulatory protein); Phospho-β-Catenin: phosphorylated (form of β-catenin degrades in the cytosol and does not translocate to the nucleus); GSK3β (glycogen synthase kinase-3β protein in the Wnt pathway phosphorylates β-catenin marking the phospo-β-catenin for rapid degradation in the protostomes); PKCβ (mediator G-protein coupled receptor); NFKβ (nuclear factor kappa B marker for inflammation when translocated to the nucleus); VEGF (vascular endothelial growth factor related to angiogenesis); E-cadherin (cell to cell interaction molecule expressed on epithelial cells, the function is lost in epithelial cancers); c-met (tyrosine kinase receptor).

In certain embodiments, the target site on the target substance is a polysaccharide antigen.

The test sample may comprise or consist of the biological sample. The biological sample in accordance with one embodiment of the invention is fluid. In an embodiment, the biological sample is a sample obtained from a biological subject, such as a sample of biological tissue or fluid origin obtained in vivo or in vitro. Suitable examples of biological samples may include, but are not limited to, blood, saliva, cerebral spinal fluid, pleural fluid, milk, lymph, sputum, semen, urine, stool, tears, needle aspirates, external sections of the skin, respiratory, intestinal, and genitourinary tracts, tumors, organs, cell cultures, or solid tissue sections. In some embodiments, the biological sample may be analyzed as is, that is, without harvest and/or isolation of the target substance of interest. In an alternate embodiment, the sample may be processed prior to mixing with the magnetic nanoparticles e.g. by harvesting of the sample prior to analysis or by the addition of suitable buffers or stabilization agents etc.

A biological sample may include any of the aforementioned samples regardless of their physical condition. In some embodiments, a biological sample may include compounds which are not naturally intermixed with the sample in nature such as preservatives, anticoagulants, buffers, fixatives, nutrients, antibiotics, or the like.

In an embodiment, the biological sample comprises blood, sputum or any body fluids or fine needle aspirates (FNA).

The method of the present invention is carried out using a magnetic resonance (MR) device. Magnetic resonance can be detected using MRI scanners, NMR spectroscopy and/or NMR relaxometry. All of these techniques have been used to measure spin-spin relaxation time ($T_2$). Clinical and experimental MRI scanners employ strong magnetic fields generated by superconducting magnets. However, MRI scanners suffer from high operation costs, bulky equipment size, and the need for large sample volumes. Benchtop relaxometers provided a more attractive alternative for point of care diagnostics (see e.g. Haun et al., Nanomedicine and Nanobiotechnology; vol. 2, issue 3, May/June 2010, pages 291-304; and Perez et al, Nat. Biotechnol. 2002, 20: pages 816-820). Benchtop systems operate at lower NMR frequencies (100 kHz-50 MHz) and are equipped with a permanent, low field magnet for field generation.

In recent years, a chip based NMR detection system (termed micro MR) has been developed to perform multiplexed diagnostic MR measurements on smaller sample volumes (see e.g. Haun et al., Nanomedicine and Nanobiotechnology; vol. 2, issue 3, May/June 2010, pages 291-304; Lee et al, Nat. Med. 2008, 14:pages 869-874; Lee et al, Proc. Natl. Acad. Sci. USA 2009, 48: pages 5657-5660; and Lee et al, Angew. Chem. Int. Ed Engl 2009, 48: pages 5657-5660).

In an embodiment, the method of the present invention is carried out using a micro MR device. In an embodiment, the micro MR device comprises one or more microcoils for both radio-frequency (RF) excitation and NMR signal detection, an NMR spectrometer, and a microfluidic network.

Figure 4:
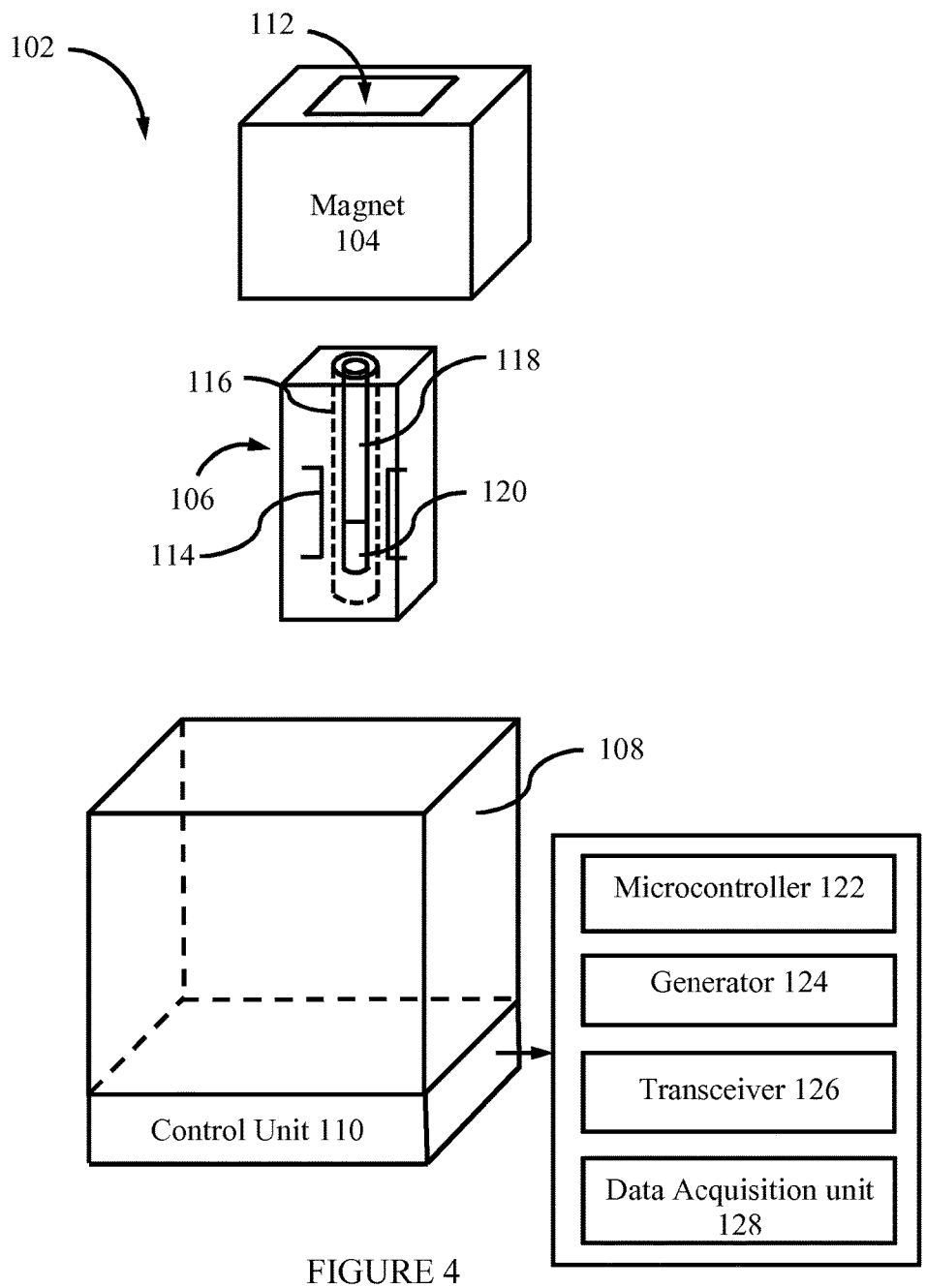
FIG. 4 is a schematic illustration of a perspective exploded view of a micro-magnetic resonance unit that may be employed in the present invention.

FIG. 4 is a schematic illustration of a perspective exploded view of a micro-nuclear magnetic resonance (MR) unit for analyzing a mixture of at least one fluid sample and nanoparticles in accordance with an embodiment. The micro-nuclear MR unit 102 is configured to receive a mixture of at least one fluid sample and nanoparticles. When the nanoparticles are subjected to a magnetic field in a micro-nuclear MR unit such as the micro-nuclear MR unit 102 they are magnetized. The magnetic moments of the nanoparticles align to the magnetic field lines and create a magnetic flux. Each nanoparticle produces a magnetic dipole that results in formation of a magnetic field gradient. The magnetic field gradient generates an inhomogeneity in a magnetic field that changes the precession frequency of nuclear spins of neighboring protons in the molecules. This results in a change in magnetic resonance signal that can be measured by a magnetic resonance imaging or nuclear magnetic resonance technique. The magnetic resonance signals measured may be considered as shortening of a longitudinal or spin-lattice relaxation time $T_1$, and transverse or spin-spin relaxation time $T_2$. The magnetic relaxation properties of the nanoparticles is dependent on particle relaxivity, and the environment of the nanoparticles e.g. whether the nanoparticles are bound or unbound to target substances such as cells/bacteria/pathogens, which can affect the transverse relaxation ($R_2=1/T_2$).

The micro-nuclear MR unit 102 includes a magnet 104, a micro-MR probe 106, a casing 108 and a control unit 110. The micro-nuclear MR unit 102 may be an integrated and portable device used for performing analysis of the mixture. The micro-nuclear MR unit 102 may have a reduced size because of the integration of miniaturized NMR system components such as the magnet 104, the micro-MR probe 106, the casing 108 and the control unit 110. The magnet 104 may be a permanent magnet or a portable permanent magnet. In an embodiment, the magnet 104 may be an assembly of a plurality of magnets to produce a higher magnetic field. The magnet 104 may be positioned around the micro-MR probe 106. In an embodiment the magnet 104 may include a pathway 112 through which the micro-MR probe 106 can be disposed to position the magnet 104 around the micro-MR probe 106. However it may be contemplated that the magnet 104 may have any other configuration to be positioned around or adjacent to the micro-NMR probe 106. The micro-MR probe 106 may be fabricated by positioning a micro-coil 114 around a micro-fluidic conduit 116. The micro-coil 114 may be a micro-coil or an array of multiple micro-coils such as, solenoid coils. For example the micro-coil 114 may be fabricated by wrapping a fine copper wire around a polyethylene tube and subsequently immersed in a polymer material such as, polydimethylsiloxane. The micro-MR probe 106 may be in a miniaturized form so may represent as a micro-MR chip. The micro-nuclear MR unit 102 comprises a high-stability permanent magnet in combination with the micro-MR coil(s) having an inner diameter in the range of 20-500 micron to increase the sensitivity of NMR detection by several orders of magnitude as compared to table-top spectrometers. It may be envisioned that micro-coils having other configurations may be used in the micro-NMR probe 106. The micro-fluidic conduit 116 is configured to receive a container 118 there within. The at least one sample and the nanoparticles may be introduced into the container 118. The at least one sample is mixed with the magnetic nanoparticles to form a mixture 120 inside the micro-fluidic conduit 116. The micro-fluidic conduit 116 provides vital functions in the sensing process, including handling of fluid samples, reproducible mixing of magnetic nanoparticles with samples, distribution of aliquots to different coil for parallel sensing and confining samples to the most sensitive region of a given micro-coil.

The magnet 104 creates a magnetic field around the micro-MR probe 106. Clusters of the nanoparticles with the target substance (e.g. cells), when present, are formed. The detection of the presence of e.g. a target cell in a fluid sample is due to the phenomenon of T2 (i.e. spin-spin relaxation time) changes from a base analyte (i.e. unreacted nanoparticle) to that when the fluid sample contains the specific target (after the nanoparticle analyte reaction is completed). Basically, after an excitation pulse, the transverse magnetization observed later decays in a characteristic exponential "free induction decay" (FID). This includes a combination of spin-spin relaxation as well as relaxation due to the presence of magnetic field in-homogeneities. When a bunch of refocusing pulses is added following a single excitation pulse, "spin echoes" are obtained. These spin echoes decay at a much slower exponential rate, termed as R2 (spin-spin relaxation rate).

The base analyte basically includes un-clustered nanoparticles that have been activated with a specific agent that binds to the target substance (e.g. a biomarker molecule). In the target cell case, these nanoparticles bind to binding sites on e.g. the cell membrane of the cell, thereby clustering the nanoparticles within close quarters of each other. The relaxation time ($T_2$) corresponding to bound nanoparticles differs from the relaxation time ($T_2$) corresponding unbound nanoparticles. The micro-coil 114 is excited through the control unit 110 for a predefined time to generate signals for example radio frequency (RF) signals and transmitted to the mixture. The mixture then generates NMR signals that decay with time. Thus this relaxation rate change for bound versus unbound nanoparticles can be used for detecting the presence of the target substance (e.g. cell) in the mixture of the sample and nanoparticles as explained above. The use of high relaxivity nanoparticles allows for detection of an extremely small number of target cells in a fluid sample, making the test a very sensitive one. The detected presence of the target cell and the target analytes in the mixture is recorded. As described in detail above, the method of the present invention can be used to detect both $T_{2bound}$ and $T_{2\ free}$ in the same sample and can further be used to quantify the amount of target substance in the sample.

The NMR signals include analysis data associated with the mixture. The NMR signals are measured by the control unit 110. The control unit 110 includes a micro-controller 122 that controls the overall operation of all the components of the control unit 110. The micro-controller 122 processes data received at the control unit 110 and communicates with external terminals for data transfer and user control. The RF signals required for transmission to the mixture are generated by a generator 124 (i.e. a RF generator) based on instructions from the micro-controller 122. The RF signals are then transmitted by a transceiver 126 such as a RF transceiver. The RF signals may be modulated using voltage controller switches present in the transceiver 126 to transmit pulse sequences for measuring the NMR signals. The NMR signals are received in the transceiver 126 and are processed for heterodyne detection. The process of heterodyne detection involves amplification at a low-noise amplifier followed by frequency down conversion to audio frequencies by a mixer. Thereafter the down converted signals are conditioned by a low-pass filter and an amplifier. These down converted signals are sent to a data acquisition unit 128 for digitization. It is also possible to bandpass filter the data and directly sample (using high fidelity, high sampling rate Analog-to-Digital Converters) at NMR frequencies. The data acquisition unit 128 includes an analog to digital converter (ADC). The ADC further converts the signal into digitized signals and thus the resultant obtained from the ADC is stored. The micro-controller 122 processes the digitized signals to obtain the analysis data and transfers to the external terminals such as a computing device. In an embodiment the control unit 110 may be integrated in an integrated circuit (IC) chip. The IC chip may be configured to support NMR measurements when there are low NMR signal levels from small fluid samples and during fast decay of signals due to an inhomogeneity caused by the magnet 104.

Further, a casing 108 of the micro-nuclear MR unit 102 may be used to cover the magnet 104, and the micro-MR probe 106 to protect these components from exposure to external environment.

Figure 5:
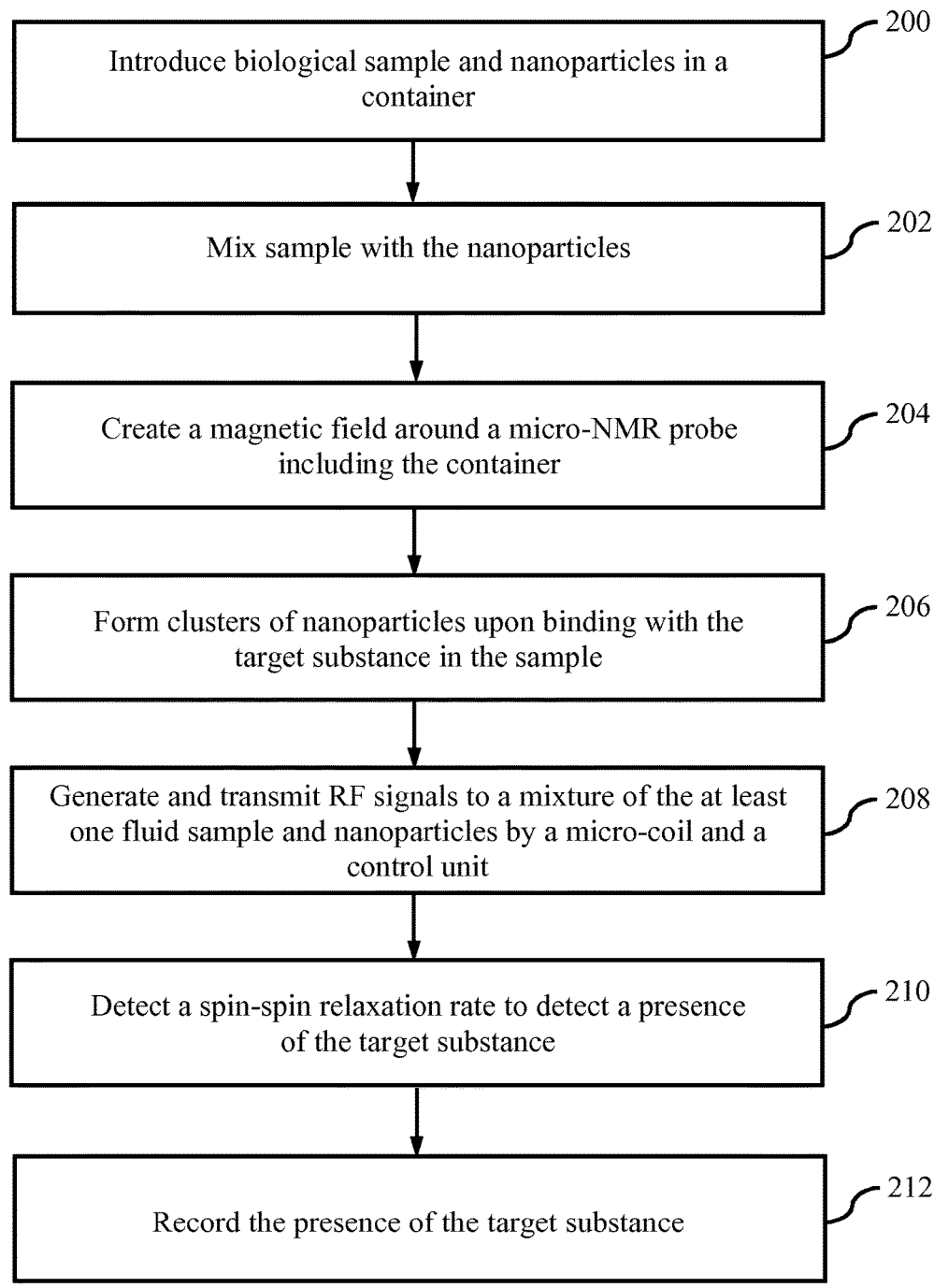
FIG. 5 is a flow diagram of a method for analyzing a mixture of a sample and nanoparticles that may be employed in the present invention.

FIG. 5 illustrates a flow diagram of a method for analyzing the mixture of the at least one test sample and the nanoparticles in accordance with an embodiment. The test sample and the nanoparticles are introduced into a container at block 200. The container is received within a micro-MR probe of a micro-nuclear MR unit. In the container, the at least one test sample and the nanoparticles are mixed at block 202. A magnet positioned proximal to the micro-MR probe is then used to create a magnetic field around the micro-MR probe holding the container at block 204. The clusters of nanoparticles are formed upon binding with the target substance (e.g. cells) in the fluid sample at block 206. A microcoil is then excited through a control unit for generating RF signals. These RF signals are transmitted to the mixture at block 208. Then, spin-spin relaxation times $T_{2bound}$ and $T_{2free}$ (or, in the alternative, the corresponding relaxation rates $R_2$ where $R_2=1/T_2$) are measured to detect the present of target substances (e.g. cells) in the mixture at block 210. The detected presence of the target substance (e.g. cells) is then recorded at block 212 and later used.

Figure 6:
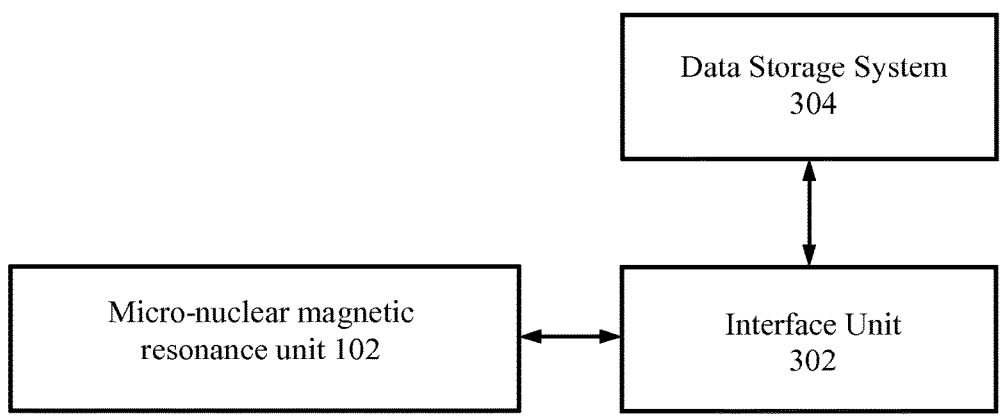
FIG. 6 is a schematic illustration of a micro-magnetic resonance system that may be employed with the present invention.

The analysis performed in the micro-nuclear MR unit may be preliminary in nature and may include, for example, tuberculosis analysis or cellular screening. The analysis data may need to be stored in a location for future use and retrieved for further examination or combined with other test results and/or data. FIG. 6 is a schematic illustration of a micro-magnetic resonance system including the micro-nuclear MR unit communicating with an interface unit in accordance with an embodiment. The analysis data obtained is received by an interface unit 302. The interface unit 302 may communicate with the micro-nuclear MR unit 102 over a network such as a wired or a wireless network. The wireless network may include but are not limited to, a Bluetooth® wireless network or a Wi-Fi® network. In another instance the analysis data may be transferred to the interface unit 302 using a universal serial bus. The interface unit 302 may be configured to process the analysis data. The analysis data received through the NMR signals may be raw digitized data associated with analysis test performed on the mixture of at least one fluid sample and the nanoparticles. The interface unit 302 processes the analysis data so as to present it to a user of the interface unit 302. The analysis data is processed to display the analysis data to a user. The user may be for example a medical expert, a doctor and an analyst associated with different applications. The analysis data may be displayed in the form of e.g. blood lipid profile, or a display of the presence or level of various biological targets or molecules in a blood sample. The analysis data may be displayed in the form of digital values and graphs. Moreover the analysis data may be processed by the interface unit 302 into a universal or standard or compatible form so that the analysis data can be integrated into other information systems.

The processed analysis data may then be transferred to a data storage system 304. The interface unit 302 communicates with the data storage system 304 over a network. The network may be a wired or a wireless network. The wireless network may include for example but not limited to, a Wide Area Network (WAN), a Wide Local Area Network (WLAN), a Local Area Network (LAN), a Wireless Metropolitan Area Network (Wireless MAN), and a cellular or a mobile network. The data storage system 304 receives and stores the processed analysis data. The processed analysis data may be then retrieved based on need. In another instance, the processed analysis data may be transferred to another computing device for further examination to conduct other medical diagnostic tests. This is explained in further detail in conjunction with FIG. 7.

Figure 7:
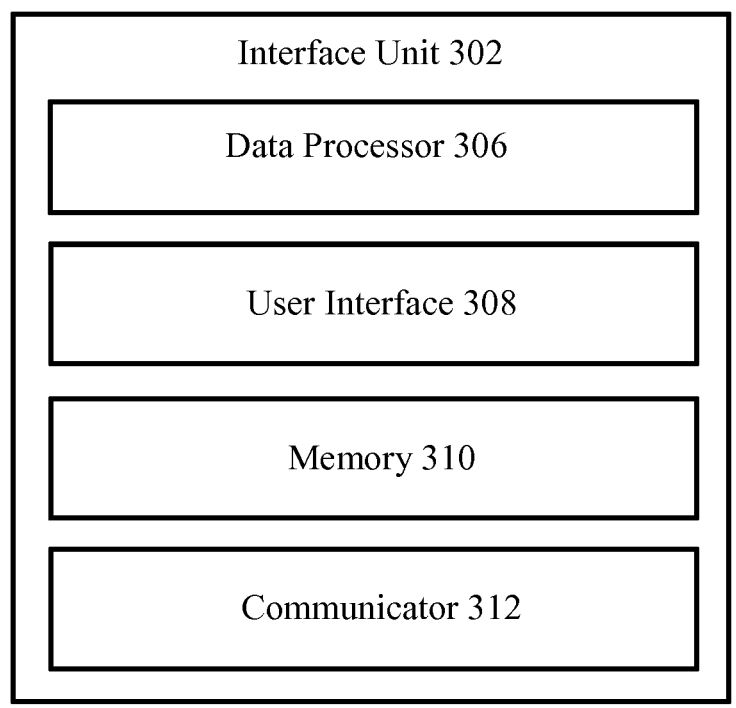
FIG. 7 is a schematic illustration of an interface unit for managing analysis data of a micro-nuclear MR unit.

FIG. 7 illustrates the interface unit for managing the analysis data of a micro-nuclear MR unit in accordance with an embodiment. The interface unit 302 may be configured in a user device such as but not limited to, a mobile device, a Personal Digital Assistant (PDA), and a personal computer. In an embodiment, the interface unit 302 may be an application operating in the user device. The interface unit 302 includes a data processor 306 configured to receive the analysis data from the micro-nuclear MR unit 102. The analysis data may be associated with different subjects (e.g. patients). The analysis data is generated in response to analysis performed on a mixture of at least one test sample and the nanoparticles for one or more different subjects in the micro-nuclear MR unit 102. The data processor 306 may be configured to control the analysis performed in the micro-nuclear MR unit 102 based on user inputs. The data processor 306 may be configured to process the analysis data to display the analysis data to a user through a user interface 308. The user may be for example a medical expert, a doctor or an analyst associated with different applications. The analysis data may be displayed in the form of e.g. blood lipid profile, or a display of the presence or level of various biological targets or molecules in a blood sample. The analysis data may be displayed in the form digital values and/or graphs.

As mentioned previously the analysis data may be received from different subjects and hence the relationship between the analysis data and the subjects may need to be established. To this end, the data processor 306 maps the processed analysis data with a subject from whom the fluid samples are obtained. The mapping is performed to define the relationship between the processed analysis data and the subject. The subject's information may be received by the data processor 306 initially when the fluid sample is received within the micro-nuclear MR unit 102. The subject's information, e.g. the patient's information, may include personal details, type of disease, health history and/or other patient demographic details.

In an embodiment the interface unit 302 receives the subject's information. The subject's information may be input through the user interface 308 by a technician or a laboratory analyst performing the analysis in the micro-nuclear MR unit 102 (shown in FIGS. 4 and 6). Once the subject's information is received, then the data processor 306 appends the subject's information to the processed analysis data associated with the at least one fluid sample of the subject. The subject's information may be appended automatically or based on user input. The processed analysis data and the appended subject's information may be stored in a memory 310 of the interface unit 302. In another embodiment, the subject's information and the processed analysis data may be stored separately. A mapping table may be present or stored, indicating a relationship between the processed analysis data and the subject's information. In an embodiment the processed analysis data and the subject's information may be encrypted. The encryption may be performed using any encryption techniques known in the art. As an example, a portion of the processed analysis data and the subject's information may be encrypted.

A communicator 312 may be present to communicate or transmit the processed analysis data (for example, the analysis data with the appended subject's information) to a data storage system such as the data storage system 304 over a network. The communicator 312 may include a transmitter and a receiver for performing the transmission and reception of data. The receiver may be configured to receive the analysis data from the micro-nuclear MR unit 102. However it may be contemplated that the communicator 312 may have any other configuration suitable for transmission and reception of data.

Figure 8:
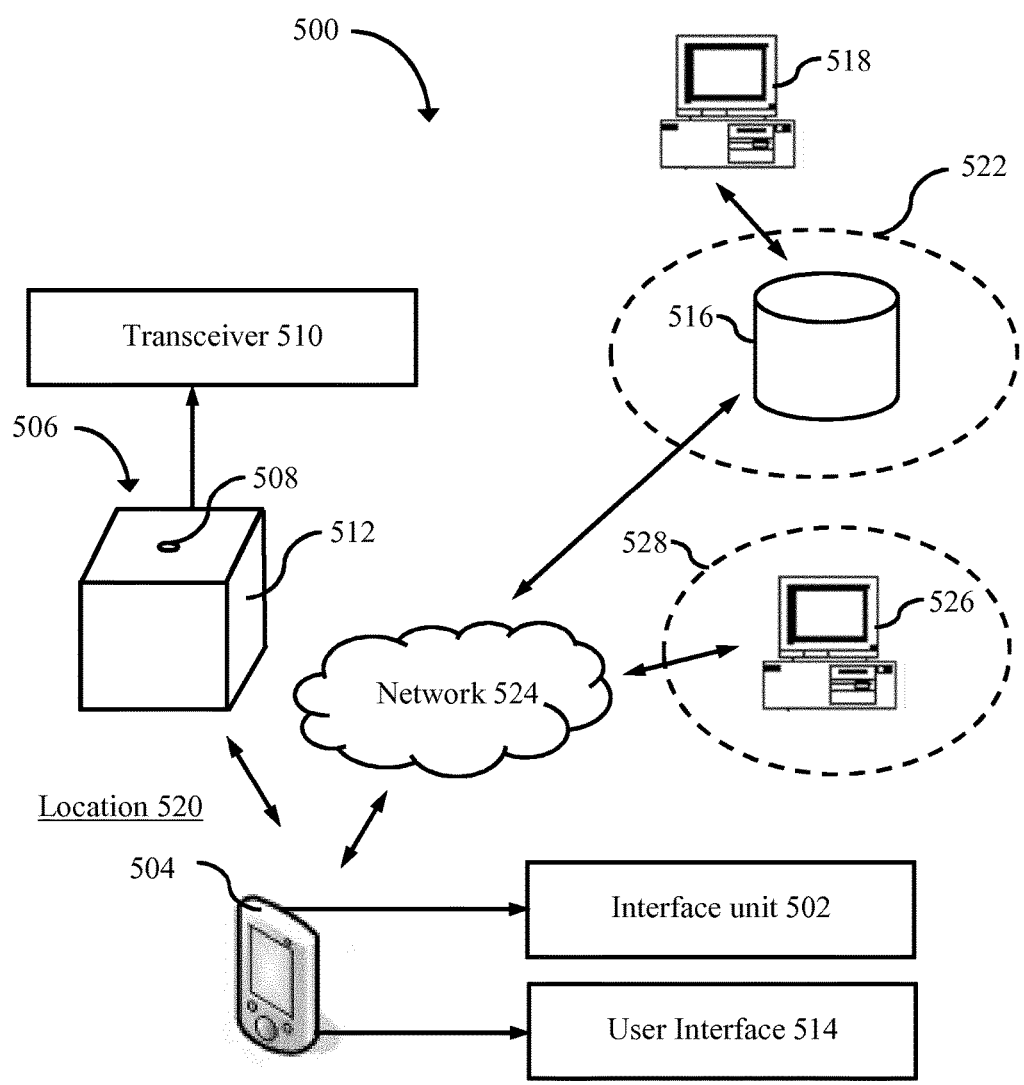
FIG. 8 is an exemplary environment for an interface unit managing analysis data generated in a micro-nuclear MR unit.

Referring now to an exemplary environment 500 illustrated in FIG. 8, an interface unit may function for managing the analysis data generated in the micro-nuclear MR unit. The interface unit 502 may be configured in a mobile device 504 communicably connected to the micro-nuclear MR unit 506. The mobile device 504 may be a PDA, a smart phone or any other devices. The micro-nuclear MR unit 506 includes an opening 508 of the micro-fluidic conduit 116 configured to receive the container holding the mixture of the at least one fluid sample and the nanoparticles. The micro-nuclear MR unit 506 analyzes the mixture. Once the analysis is conducted, the analysis data is communicated to the interface unit 502 in the mobile device 504 by a transceiver 510 in the micro-nuclear MR unit 506. The micro-nuclear MR unit 506 may be subjected to different external interferences such as radio frequency (RF) interferences and thus the analysis data generated may be error prone. Hence an interference shield 512 may be disposed around the micro-nuclear MR unit 506 to shield the interferences incident on the unit. The interference shield 512 act as a "faraday's cage" provided externally and may assist in overcoming electromagnetic interference due to the low-power radio frequency signals transmitted and received. In an embodiment the interference shield 512 may be a box covering that encloses the micro-nuclear MR unit there within. For example the interference shield 512 may be configured to enclose a magnet, and a micro-MR probe of the micro-nuclear MR unit 506. The interference shield 512 may be a metallic shield for example a copper shield, an aluminum shield, a Mu-metal shield, permalloy shield, and nano-crystalline grain structure ferromagnetic metal shield. However it may be contemplated that interference shield 512 may be composed of other known materials capable of shielding different kinds of interferences. For instance, the interference shield 512 also facilitates in avoiding the exposure of components in the micro-nuclear MR unit 506 to dust and other foreign particles. The interface shield 512 may have any other structure or configuration convenient for shielding the micro-nuclear MR unit 506. In an embodiment the interference shield 512 may have a box shape configuration, for example having a size of 7.5 cm×7.5 cm×5 cm (Length×Breadth×Width).

Subsequently, the interface unit 502 processes the analysis data and displays the processed analysis data through the user interface 514. The interface unit 502 may also map the processed analysis data with a subject of the analysis data. Thereafter, the processed analysis data may be transferred to a data storage system 516 for storage. The stored data may be retrieved when needed by the user based on the user input received in the mobile device 504. The processed analysis data may be accessed through any other computing device capable of communicating with the data storage system 516. The processed analysis data may be communicated from the mobile device 504 to a computing device 518 for further analysis. The processed analysis data may be stored in a storage unit (not shown) of the computing device 518. The computing device 518 may be located in a laboratory where more detailed analysis may be performed.

For example, a user may use the micro-nuclear MR unit 506 for analyzing at least one mixture of test sample and nanoparticles in a location 520. The mixture may be collected from a subject whose health needs to be analyzed. Analysis data associated with the analysis performed may be sent to the mobile device 504 of the user. The analysis data may be transmitted over a connection between the mobile device 504 and the micro-nuclear MR unit 506. The connection may be a Wi-Fi® or a Bluetooth® connection and hence the mobile device 504 may be positioned proximal to the micro-nuclear MR unit 506. The interface unit 502 in the mobile device 504 may process the analysis data and display the processed analysis data to the user. The processed analysis data may be displayed through the user interface 514 provided. The interface unit 502 appends the subject's information with the processed analysis data and communicates with the data storage system 516 in a location 522 in real-time. The subject's information acts as a metadata appended to the processed analysis data. Thus, the metadata may include, for example, a patient's information such as, but not limited to, personal details, type of disease, health history and other patient demographic details. The processed analysis data may be transferred over a network 524 such as a Wide Area Network (WAN), a Wide Local Area Network (WLAN), a Local Area Network (LAN), a Wireless Metropolitan Area Network (Wireless MAN), and a cellular or a mobile network. The processed analysis data may be later transferred based on user input received through the interface unit 502. The user input may be submitted by the user through the user interface 514. In an embodiment interface unit 502 may also enable the user to retrieve the processed analysis data from the data storage system 516.

The interface unit 502 may also be configured to transmit the processed analysis data to a computing device 526 present in a location 528 in real-time. The transmission of data may be performed in response to receiving user instructions through the mobile device 504. The computing device 526 may perform detailed analysis on the processed analysis data. In an embodiment, the interface unit 502 may be configured to receive the detailed analysis and present to the user in the location 520. Thus the interface unit 502 facilitates the user to transfer the processed analysis data conveniently from the location 520 to the location 522 that is remotely located. In this way, preliminary processing of the analysis data may be performed locally in the field by the user using the mobile device 504 and the micro-nuclear MR unit 506, and then later transferred to a remote location where the processed analysis data may be stored or further analyzed in a laboratory.

Figure 9:
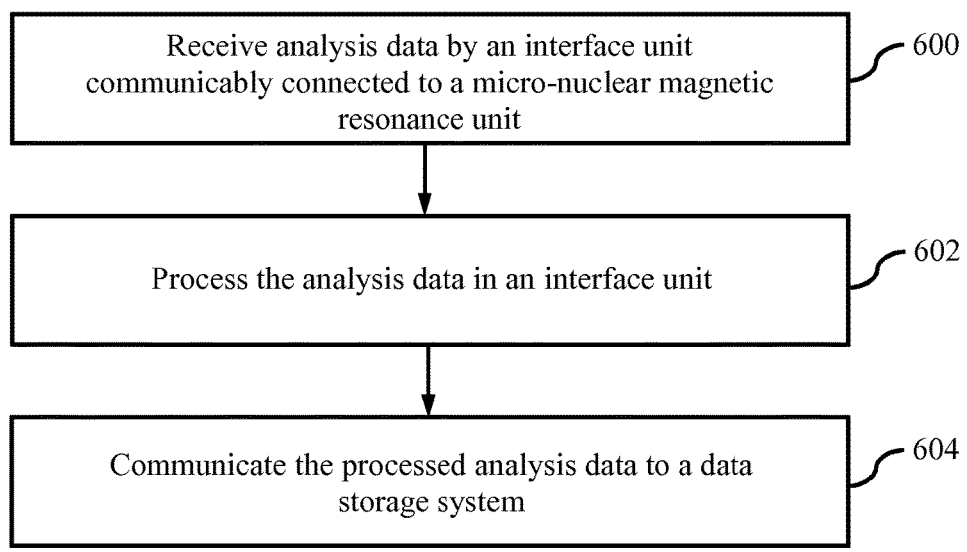
FIG. 9 illustrates a flow diagram of a method of managing analysis data in a micro-magnetic resonance unit.

FIG. 9 illustrates a flow diagram of a method of managing analysis data in a micro-magnetic resonance unit. The analysis data is generated when the mixture of test sample and nanoparticles for one or more different subjects are analyzed in a micro-nuclear MR unit. The analysis data may be transmitted to an interface unit communicably connected to the micro-nuclear MR unit. The interface unit receives the analysis data at block 600.

The interface unit then processes the analysis data at block 602. The analysis data may be processed and presented or displayed to a user. The user may be, for example, a medical expert, a doctor or an analyst. For example the interface unit may provide a user interface in a user device through which the processed analysis data may be displayed. The processed analysis data may be communicated to a data storage system for storage and retrieval at block 604. The data storage system may be remotely located, for example, in a laboratory. The processed analysis data stored may be retrieved based on user input received through the interface unit in the user device. The user input may be sent as instructions to the data storage system. The processed analysis data may be retrieved by any other computing device that may be configured to perform more analysis using the processed analysis data of the mixture(s).

Figure 10:
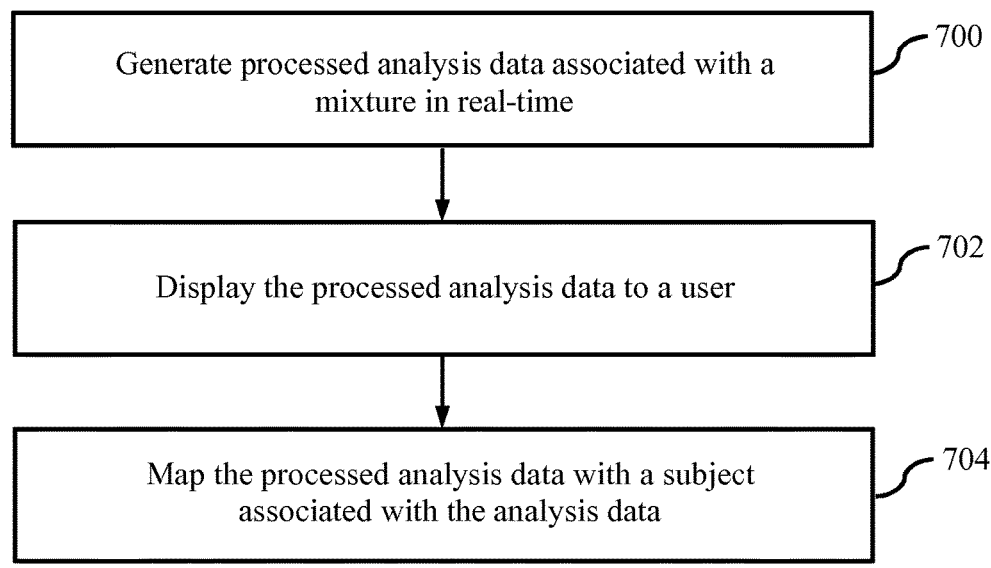
FIG. 10 illustrates a flow diagram of a method of processing the analysis data in the interface unit.

FIG. 10 illustrates a flow diagram of a method of processing the analysis data in the interface unit in accordance with an embodiment of the invention. The analysis data received from the micro-nuclear MR unit is processed in the interface unit at block 700 to generate the processed analysis data. The processed analysis data is presented or displayed to the user at block 702. The analysis data may be processed in real-time. More specifically, the analysis data may be received from the micro-nuclear MR unit and processing may be performed in the interface unit and presented or displayed to the user through the user device. This enables the user to view the analysis results conveniently in real-time when the analysis of the at least one fluid sample is conducted. The analysis data may be processed to enable the presentation of the analysis data in form of e.g. blood profile or the presence/absence or amount of various biological targets (e.g. cells, bacteria or pathogens) in the biological (e.g. blood) sample.

The processed analysis data may be mapped with a subject associated with the analysis data at block 704. The sample may be obtained from the subject. The mapping is performed to define the relationship between the processed analysis data and the subject. The subject's information may be received through the interface unit when the at least one fluid sample is received within the micro-nuclear MR unit. The subject's information may include e.g. personal details, disease type, health history and other patient demographic details.

The subject's information may be received through the interface unit. For example, the subject's information may be input through the user device by a technician or a laboratory analyst performing the analysis in the micro-nuclear MR unit. The subject's information received may be appended to the processed analysis data associated with the at least sample of the subject. The subject's information may be appended automatically. The subject's information may be appended based on user input. In another embodiment, the subject's information and the processed analysis data may be stored separately. A mapping table may be present or stored in this case indicating a relationship between the processed analysis data and the subject's information. The processed analysis data and the subject's information may be encrypted. The encryption may be performed using any techniques known in the art. In an embodiment, a portion of the processed analysis data and the subject's information may be encrypted. The processed analysis data and the subject's information may be stored in the user device for future use.

Figure 11:
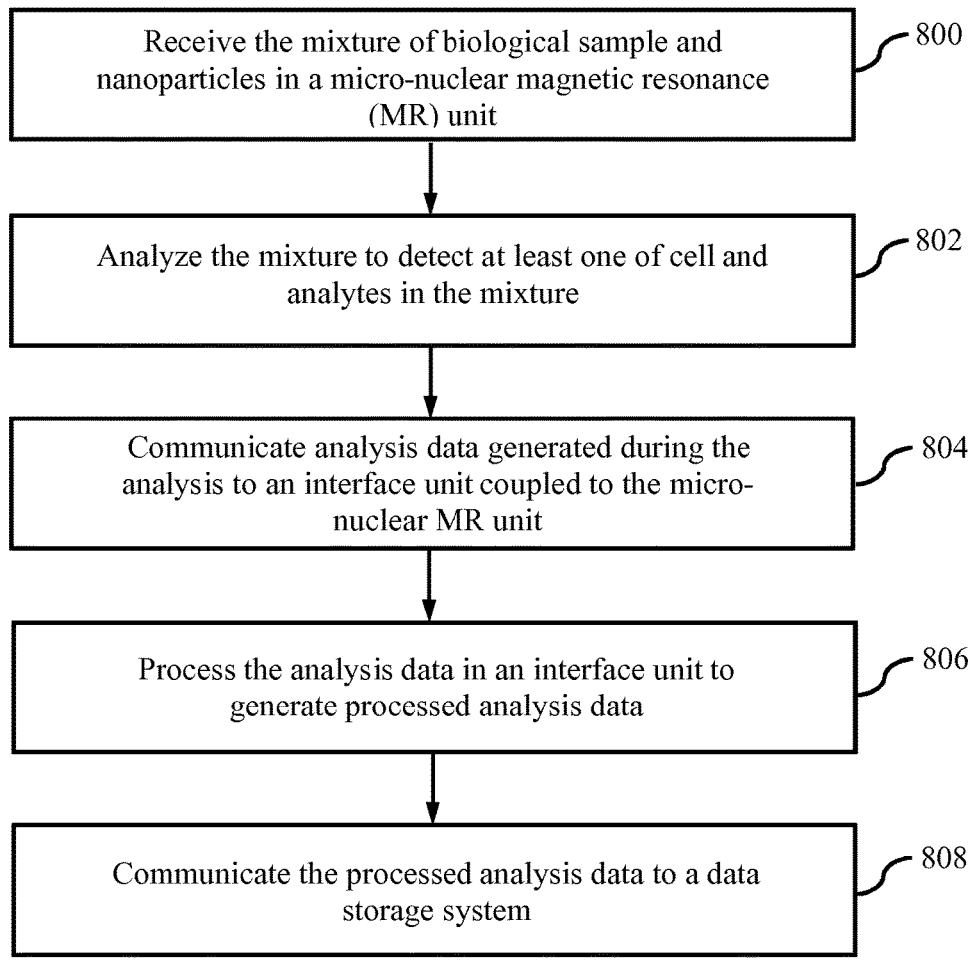
FIG. 11 illustrates a flow diagram of a method of analyzing a mixture of at least one fluid sample and nanoparticles using a micro-magnetic resonance system in accordance with an embodiment.

FIG. 11 illustrates a flow diagram of a method of analyzing a mixture of at least one sample and nanoparticles using a micro-magnetic resonance system in accordance with an embodiment of the invention. A micro-nuclear magnetic resonance (MR) unit of a micro-magnetic resonance system receives the mixture of the at least sample and the nanoparticles at block 800. The mixture is formed in a container that may be received within a micro-fluidic conduit of the micro-nuclear MR unit. The mixture is then analyzed by the micro-nuclear MR unit to detect at least one target substance (e.g. cell) in the mixture at block 802.

The analysis data generated by the analysis performed on the mixture may be communicated to an interface unit communicably connected to the micro-nuclear MR unit at block 804. The interface unit receives the analysis data and then processes the analysis data at block 806. The analysis data may be processed, and then presented or displayed to a user. The user may be, for example, a medical expert, a technician or a doctor. For example, the interface unit may provide a user interface in a user device through which the processed analysis data may be displayed. The processed analysis data may be communicated to a data storage system for storage and retrieval at block 808. The data storage system may be remotely located, for example in a laboratory. The processed analysis data stored may be retrieved based on user input received through the interface unit in the user device. The user input may be sent as instructions to the data storage system. The processed analysis data may be collected by any other computing device communicably connected to the data storage system. The computing device may be configured to perform more analysis using the processed analysis data for conducting detailed analysis of the mixture of the at least one sample and the nanoparticles.

The methods described with respect to FIG. 9, FIG. 10 and FIG. 11 may be performed using a processor or any other processing device. The method steps can be implemented using coded instructions (e.g., computer readable instructions) stored on a tangible computer readable medium. The tangible computer readable medium may be for example a flash memory, a read-only memory (ROM), a random access memory (RAM), or any other computer readable storage medium or any storage media. Although the method of managing the analysis data generated in a micro-nuclear MR unit is explained with reference to the flow chart of FIGS. 9, 10 and 11, other methods of implementing the method can be employed. For example, the order of execution of each method steps may be changed, and/or some of the method steps described may be changed, eliminated, divide or combined. Further the method steps may be sequentially or simultaneously executed for managing the analysis data generated in a micro-nuclear MR unit.

The present invention will now be described with reference to the following non-limiting examples.

EXAMPLES

Material and Methods

The carboxyl functionalized Super Paramagnetic Iron Oxide (SPIO) nanocrystal and its conjugation kit were procured from Ocean NanoTech LLC, USA. The Rabbit polyclonal antibody raised from *Bacillus cereus*, that is cross-reactive to *Bacillus subtilis* (ab20556) was purchased from Abcam, USA. *Bacillus subtilis* subsp. *spizizenii* (*B.* subtilis) was purchased (ATCC #6633) from HiMedia Laboratories, Mumbai, India and maintained according to the vendor's protocols.

Synthesis and Characterization of SPIO-bacillus Antibody

Antibody that reacts with *Bacillus subtilis* was conjugated to carboxyl terminal SPIO nanoparticles (size=30 nm) by following the manufacturer's protocol. Briefly, stock solution of 1-ethyl-3-(3-dimethylaminopropyl) carbodiimide (EDC)/N-hydroxysuccinimide (NHS) was prepared as per manufacturer's instructions yielding a final concentration of 2 mg/mL EDC and 1 mg/mL NHS. 100 µL of SPIO was taken in 50 µL of activation buffer in an eppendorf tube and 50 µL of EDC/NHS solution was added to it. The mixture was reacted at room temperature (RT) for 10 min with continuous mixing. To the activated SPIO nanoparticles, 250 µL of the coupling buffer was added followed by the addition of 4 µg of antibody that reacts with *Bacillus subtilis*. The mixture was allowed to react at RT with continuous mixing for 2 h. At the end of the 2 h, the reaction was arrested by adding 5 µL of quenching buffer. The nanoconjugate was separated from the free SPIO nanoparticles by filtration of the reaction mixture using 100 kDa molecular weight cut off Amicon filter and washed with storage buffer (2×1 mL). The size of the final conjugate used in this study was measured via dynamic light scattering (Zetasizer Nano-ZS, Malvern) and exhibited an average hydrodynamic diameter of 45 nm. Iron concentration of the nanoconjugate solution was measured to be 250 µg/mL using an Agilent 7500cx Inductively Coupled Plasma-Mass Spectrometry (ICP-MS) instrument.

Preparation of Media for Bacterial Culture 0.4 g of Difco™ Nutrient Broth (Ref 234000, BD) was transferred to a 250 mL conical flask and dissolved in 50 mL of DM water. The resulting solution was autoclaved at 121° C. for 15 minutes. The cooled flask with the media was then used for culturing.

Culturing of *B. subtilis*

The *B. subtilis* stock culture and the nutrient broth solutions were placed in the incubator at 37° C. for 10-15 minutes. The flasks were then transferred to the laminar air flow hood. From the stock, 500 µL was pipetted carefully into 50 mL of nutrient broth, maintaining sterile conditions. The flask was then placed in the Innova 4080 incubator-shaker set at 37° C. at 115 rpm for 6 hours. The count of bacteria after 6 hours of incubation was determined by standard plate count method and was found to be ~$10^8$ CFU/mL.

Serial Dilution and Sample Preparation

Serial dilutions were carried out on the 6 hour *B. subtilis* culture to obtain $10^7$, $10^5$ and $10^3$ concentration of bacteria.
64 µL of the 250 µg/mL Fe nanoconjugate solution was added to 1 mL each of $10^7$, $10^5$ and $10^3$ *B. subtilis* samples to obtain a final concentration of 16 µg/mL of Fe in the mixture. T2 relaxation measurements were performed immediately after mixing.

Relaxometer Measurements

Relaxation time measurements were performed at 40° C. using a Bruker mq20 Minispec at 0.5 T. The data was acquired at regular time intervals, every 1 min for the first 9 time points, then every 5 min for the next 6 time points, every 10 min for the next 6 time points, every 15 min for the next 3 time points and eventually every 30 min for the last 3 time points. For the T2 relaxation time measurements, the pulse sequence employed is the Carr-Purcell-Meiboom-Gill (CPMG) spin echo.
CPMG Pulse Sequence:

$$\{RD-90_0\text{-tau-}[(180_{90}\text{-tau-})DE(180_{90}\text{-tau-})\text{asd-tau-}]_N\}_{NS}$$

where:
RD is the recycle delay, tau is a delay interval, DE is the number of dummy echoes before an echo is sampled, N is the number of points to be collected, NS is the number of scans for signal averaging, and "asd" is indicative of acquisition of a single data point.
The following parameters were used for the experiments; RD=6 s; tau=5 ms, DE=0, N=700, NS=8.
The data from the spin echo was fitted to a bi-exponential equation as given below:

$$y = A1 * \exp(-(x/\tau 1)) + A2 * \exp(-(x/\tau 2)) + O$$

where:
A1, A2=amplitudes of components 1 and 2 at time zero
$\tau 1$, $\tau 2$=T2 decay constants of components 1 and 2
O=offset

RESULTS

In all samples, after addition of nanoconjugates to the different concentrations of *B. subtilis*, a bi-exponential T2 was observed. FIG. 1 shows the change in T2 with time for the mixtures of SPIO-nanoconjugates and different concentrations of bacteria. The long T2 obtained after 2 h was similar to the one observed in experiments where a complete sample preparation was performed. Thus the long T2 was assigned to the nanoconjugates bound to the bacteria and the short T2 to the nanoconjugates that are unbound or free in the solution. In addition, it was also observed that the long T2 of the bound nanoconjugates is dependent on the concentration of the bacteria. Thus it is possible to quantitate the number of bacteria in the sample just using the long T2 without requiring a filter step to filter the unbound nanoconjugates.

What is claimed is:
1. An in-vitro method for detecting a presence of a target substance in a biological sample by magnetic resonance, the in-vitro method comprising:
providing a mixture sample comprising the biological sample and a plurality of magnetic nanoparticles, wherein the magnetic nanoparticles comprise a binding agent capable of binding the target substance, and a cluster of magnetic nanoparticles is formed upon binding of the magnetic nanoparticles with the target substance when the target substance is present in the biological sample;
determining, when both the formed cluster of magnetic nanoparticles bound to the target substance and the magnetic nanoparticles not bound to the target substance are present in the mixture sample, and without physically separating the cluster of magnetic nanoparticles and the magnetic nanoparticles not bound to the target substance, two separate $T_2$ values from said mixture sample, the two separate $T_2$ values corresponding to $T_{2bound}$ and $T_{2free}$, wherein $T_{2bound}$ is a $T_2$ spin-spin relaxation time of protons of water molecules surrounding the cluster of magnetic nanoparticles bound to the target substance, and $T_{2free}$ is a $T_2$ spin-spin relaxation time of protons of water molecules surrounding the magnetic nanoparticles not bound to the target substance;

wherein the determining step further comprises:

providing NMR data of the mixture sample subjected to a multi-echo spin-echo pulse sequence, and determining the two separate $T_2$ values corresponding to $T_{2bound}$ and $T_{2free}$ by applying a bi-exponential fit to the NMR data of the mixture sample.

2. The in-vitro method according to claim 1, wherein the target substance is a cell, a pathogen, or a bacterial cell.

3. The in-vitro method according to claim 1, wherein the bi-exponential fit is applied using:

$$y = A1*\exp-(x/\tau 1) + A2*\exp-(x/\tau 2) + O \quad \text{(equation 1)}$$

where:

A1, A2=amplitudes of components 1 and 2 at time zero, $\tau 1$, $\tau 2$=T2 decay constants of components 1 and 2, O=offset.

4. The in-vitro method according to claim 1, further comprising quantitating the amount of target substance in the biological sample, wherein the value of $T_{2bound}$ is dependent on the amount of target substance in the biological sample, and the amount of target substance in the biological sample is determined by comparing the value of $T_{2bound}$ with a standard plot of $T_{2bound}$ values measured at different concentrations of target substance.

5. The in-vitro method according to claim 1, wherein the value of $T_{2bound}$ is dependent on the amount of target substance in the biological sample, and the value of $T_{2bound}$ is compared to one or more standard values obtained from reference samples comprising known amounts of target substance.

6. The in-vitro method according to claim 1, wherein the method is carried out on a micro-MR device.

7. The in-vitro method according to claim 1, wherein the magnetic nanoparticles comprise superparamagnetic particles conjugated to the binding agent.

8. The in-vitro method according to claim 1, wherein the magnetic nanoparticles comprise a core comprising superparamagnetic iron oxide, and the binding agent conjugated to the nanoparticles.

9. The in-vitro method according to claim 1, where the binding agent is an antibody or an antibody fragment comprising a binding site specific for the target substance.

10. The in-vitro method according to claim 1, wherein the biological sample is obtained from an individual, wherein the individual is suspected of having a disease or an infection, and wherein detection of the target substance is indicative of the disease or the infection.

11. A method for detecting a presence of a target substance in a biological sample, the method comprising:

(a) providing NMR data from a mixture sample comprising the biological sample and a plurality of magnetic nanoparticles, wherein the magnetic nanoparticles comprise a binding agent capable of binding the target substance, and a cluster of magnetic nanoparticles is formed upon binding of the magnetic nanoparticles with the target substance when the target substance is present in the biological sample; and (b) processing the NMR data to determine if different $T_2$ values corresponding to $T_{2bound}$ and $T_{2free}$ are present, wherein $T_{2bound}$ is a $T_2$ spin-spin relaxation time of protons of water molecules surrounding the cluster of magnetic nanoparticles bound to the target substance if present, and $T_{2free}$ is a $T_2$ spin-spin relaxation time of protons of water molecules surrounding magnetic nanoparticles not bound to the target substance, wherein the method further comprising:

providing NMR data of the mixture sample subjected to a multi-echo spin-echo pulse sequence, and determining, when both the formed cluster of magnetic nanoparticles bound to the target substance and the magnetic nanoparticles not bound to the target substance are present in the mixture sample, and without physically separating the cluster of magnetic nanoparticles and magnetic nanoparticles not bound to the target substance, two separate $T_2$ values from said mixture sample, the two separate $T_2$ values corresponding to $T_{2bound}$ and $T_{2free}$ by applying a bi-exponential fit to the NMR data of the mixture sample.

* * * * *